US008846035B2

(12) United States Patent
Bohmer et al.

(10) Patent No.: US 8,846,035 B2
(45) Date of Patent: Sep. 30, 2014

(54) METHODS FOR PREPARING POLYMER MICROPARTICLES

(75) Inventors: Marcel Rene Bohmer, Eindoven (NL); Johannes Antonius Maria Steenbakkers, Eindhoven (NL); Suzanna Helena Petronella Maria De Winter, S-Hertogenbosch (NL); Anne Bechet, Alphen Aan Den Rijn (NL); Rudolf Verrijk, Noordwijk (NL)

(73) Assignee: Koninklijke Philips N.V., Eindhoven (NL)

( * ) Notice: Subject to any disclaimer, the term of this patent is extended or adjusted under 35 U.S.C. 154(b) by 632 days.

(21) Appl. No.: 12/738,320

(22) PCT Filed: Oct. 21, 2008

(86) PCT No.: PCT/IB2008/054324
§ 371 (c)(1),
(2), (4) Date: Apr. 16, 2010

(87) PCT Pub. No.: WO2009/053900
PCT Pub. Date: Apr. 30, 2009

(65) Prior Publication Data
US 2010/0209525 A1   Aug. 19, 2010

(30) Foreign Application Priority Data
Oct. 23, 2007   (EP) .................................... 07119109

(51) Int. Cl.
| A61K 9/14 | (2006.01) |
| A61K 47/32 | (2006.01) |
| B01J 2/08 | (2006.01) |
| A61K 9/16 | (2006.01) |
| B01J 2/06 | (2006.01) |
| B01J 2/18 | (2006.01) |

(52) U.S. Cl.
CPC ................. *A61K 9/1647* (2013.01); *B01J 2/08* (2013.01); *A61K 9/1635* (2013.01); *A61K 9/1641* (2013.01); *B01J 2/06* (2013.01); *B01J 2/18* (2013.01)
USPC ................. 424/124; 424/501; 425/6; 425/10; 264/5; 264/14

(58) Field of Classification Search
CPC . A61K 9/1635; A61K 9/1641; A61K 9/1647; B01J 2/06; B01J 2/08
USPC ........ 264/14, 5; 425/10, 6; 424/501; 418/124
See application file for complete search history.

(56) References Cited

U.S. PATENT DOCUMENTS

| 6,599,627 | B2 | 7/2003 | Yeo et al. |
| 6,669,916 | B2 | 12/2003 | Heim et al. |
| 6,669,961 | B2 | 12/2003 | Kim et al. |
| 6,767,637 | B2 | 7/2004 | Park et al. |
| 6,998,074 | B1 | 2/2006 | Radulescu |
| 2002/0054912 | A1 | 5/2002 | Kim et al. |
| 2002/0160109 | A1 | 10/2002 | Yeo et al. |
| 2003/0230819 | A1 | 12/2003 | Park et al. |
| 2004/0166124 | A1 | 8/2004 | Dunfield et al. |

FOREIGN PATENT DOCUMENTS

| DE | 4338212 A1 | 5/1995 |
| EP | 0830859 A2 | 3/1998 |
| EP | 1090928 A1 | 4/2001 |
| EP | 1247522 A1 | 10/2002 |
| EP | 1679065 A1 | 7/2006 |
| WO | 03079990 A1 | 10/2003 |
| WO | 03079990 A2 | 10/2003 |
| WO | 2006003581 A1 | 1/2006 |

OTHER PUBLICATIONS

Choy et al. (Macromolecular Bioscience, vol. 7, Issue 4, Published online Apr. 11, 2007, pp. 423-428).*
Berkland et al: "Fabrication of PLG Microspheres With Precisely Controlled and Monodisperse Size Distributions"; Journal of Controlled Release, Vol. 73 (2001), pp. 59-74.
Bohmer et al: "Preparation of Monodisperse Polymer Particles and Capsules by Ink-Jet Printing"; Colloids and Surfaces A:Phyicochem. Eng. Aspects, vol. 289 (2006), pp. 96-104.
Radulescu et al: "Uniform Paclitaxel-Loaded Biodegradable Microspheres Manufactured by Ink-Jet Technology"; Controlled Release Society's 11th International Symposium on Recent Advances in Drug Delivery Systems, Salt Lake City, Utah, 2003, 5 Page Document.

* cited by examiner

*Primary Examiner* — Richard Schnizer
*Assistant Examiner* — Alma Pipic

(57) ABSTRACT

The present invention describes methods and tools for preparing a population of monodisperse polymer microparticles, which are of particular interest in the field of drug delivery.

13 Claims, 5 Drawing Sheets

METHODS FOR PREPARING POLYMER MICROPARTICLES

FIELD OF THE INVENTION

The present invention relates to methods for producing monodisperse microparticle populations particularly suitable for drug delivery as well as to the dispersions themselves and also to use of the dispersions for drug delivery.

BACKGROUND OF THE INVENTION

In many drug delivery applications a strict control of the particle size and particle size distribution is required. An example is the delivery of drug-releasing particles from a catheter, more particularly where delivery into the capillary bed of a tumour such as a liver tumour is required. In this application of drug delivery, the particles are supposed to embolise in the smallest capillaries from where they can release drugs, such as cytostatics or provide local $\beta$ or $\gamma$ radiation. This is the case for particles loaded with Holmium acetyl-acetonate. The size of the particles plays an important role in the efficacy of the treatment. If the particles are too small, they will circulate and accumulate in other areas, for instance the lungs. If they are too big, they will not reach the smallest capillaries. Therefore the most effective therapy will be achieved with precisely and uniformly tailored particles.

One way to arrive at very well-defined particles derived from biodegradable polymers is to use a technique in which a liquid with the dissolved polymer and the drug is pushed through a capillary whereby the liquid jet is broken up into droplets, for instance by application of a frequency from a piezo-element or similar devices. Such systems have been described in U.S. Pat. No. 6,669,916, U.S. Pat. No. 6,998,074 and WO2006/003581 and Berkland et al. (2001) *J. Control. Release* 73, 59-74. In U.S. Pat. No. 6,669,916 the jetting is accompanied by an additional downward force or acceleration to make it possible to produce droplets that are smaller than the nozzle diameter. An example of such a downward force is a co-flowing stream of a solution of polyvinylalcohol. A problem noted in U.S. Pat. No. 6,669,961 is the generation of particles from nozzles that are smaller than 30 μm in diameter, which get clogged easily. The technology disclosed in U.S. Pat. No. 6,669,961 allows the use of fairly concentrated solutions (5% of polymer) for the production of particles in the desired size range. However, because of the additional force that is needed, the production system becomes more complicated. Moreover for particles significantly smaller than 50 μm the size distributions are wider than for particle above 50 μm. A similar carrier stream, intended to encapsulate for instance an aqueous phase, rather than splitting up the stream in smaller droplets has been disclosed in U.S. Pat. No. 6,599,627. This technique generates relatively large capsules, i.e. larger than 100 μm.

Particles with a size of 65 μm have been produced using drop-on-demand nozzles of 65 μm as described by Radulescu et al. (2003, *Proc. 11$^{th}$ Int. Symp. Control. Rel. Soc*). Herein, an assistant pressure can be applied to enhance the production speed. U.S. Pat. No. 6,998,074, from the same research group, describes the use of a drop-on-demand ink-jet method without assistant pressure, with a nozzle submerged in a liquid to fabricate polymer microspheres.

WO2006/003581 describes that smaller particles than those known in the art can be produced using a submerged nozzle to which a frequency is applied, preferably in combination with an assistant pressure. Careful shrinkage of the jetted emulsion droplets yielded particles as small as 2 μm. Monodisperse hollow capsules could be obtained as also described in Böhmer et al. (2006) (*Colloids and Surfaces* 289, 96-104). In the described system, an assistant pressure not only allows higher jetting rates but also prevents clogging of the nozzle of the device. If no additional pressure is used, polymers such as poly-lactic acid, will precipitate at the interface between the fluid to be jetted and the continuous phase. The process is described in WO2006/003581 uses lower polymer concentration than the process described in U.S. Pat. No. 6,669,961 or U.S. Pat. No. 6,767,637, resulting in the shrinkage of the emulsion droplets to smaller sizes.

All methods described in the prior art documents cited above make use of additives such as polyvinylalcohol to stabilize the emulsion droplets and the resulting particles. The addition of polyvinylalcohol has two effects on the preparation of polymer particles from biodegradable polymers. It stabilises both the emulsion droplets and the particles formed therefrom.

Besides issues of size and uniformity, another problem in inkjetting particles is the fragility of emulsion droplets in the receiving fluid. Stirring during solvent extraction has to occur very gently, otherwise the droplets break-up easily. Böhmer et al. (2006) *Colloids & Surfaces, Physicochem. Eng. Aspects* 289, 96-104 describes a system wherein microparticles are not stirred after release from a nozzle.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

One aspect of the present invention relates to methods for preparing monodisperse hydrogel polymer microparticles with a size ranging between 1 and 100 μm more particularly 1 and 50 μm wherein these microparticles comprise a bioactive agent, which comprise the steps of (a) preparing an emulsion of a hydrogel forming polymer comprising the bioactive agent, (b) ejecting droplets of the emulsion of step (a) from a nozzle submerged in an aqueous receiving fluid using an assistant pressure and applying a frequency, and (c) allowing the droplets to form into microparticles by keeping them within the receiving fluid for a time period sufficient to remove solvent from said droplets and allow incorporation of water within said droplets.

This is preferably performed by swelling and hardening the droplets into microparticles by allowing the droplets to move within the receiving fluid for a time period which ensures removal of solvent and saturation with water of the droplets.

In one embodiment of the methods according to this aspect of the invention, the concentration of polymer is between 1-3%, the diameter of the nozzle is between 1-50 μm and the time period that the droplets are moved within the receiving fluid is between 2 and 60 seconds.

In a particular embodiment of these methods, step (c) is ensured without agitation of the microparticles within the receiving fluid.

In a further particular embodiment of these methods, the formation of microparticles in step (c) is performed by allowing the particles to move within the receiving fluid down an inclined surface having a slope of at least 10 degrees. In this step (c) preferably swelling and hardening takes place.

In yet another embodiment of these methods, the inclined surface has a gradually changing slope.

Another aspect of the present invention relates to methods for preparing monodisperse polymer microparticles with a size ranging between 1 and 100 μm and more particularly between 1 and 50 μm wherein these microparticles comprise a bioactive agent, which methods comprise the steps of (a) preparing an emulsion of the bioactive agent and a solution of a polymer, (b) injecting particles or droplets of the emulsion of step (a) from a nozzle submerged in a receiving fluid, using an assistant pressure and applying a frequency, and (c) hardening these particles or droplets into microparticles by allowing the particles to move, within the receiving fluid on an inclined surface, wherein the slope of the inclined surface is a gradually changing slope and wherein the slope at each point has an angle of at least 10 degrees, more particularly at least 20 degrees.

In a particular embodiment of these methods, the polymer is a hydrogel polymer. In those embodiments the methods according to this aspect of the invention, wherein the polymer used is a hydrogel polymer, further particular embodiments are envisaged wherein step (c) comprises the step of allowing the particles to move, within the receiving fluid on the inclined surface for a time period which ensures the removal of solvent and saturation with water.

In a particular embodiment of the methods above, the concentration of the hydrogel polymer in the emulsion is adjusted in order to obtain hydrogel particles with a diameter which is more than 40%, more particularly more than 65% of the diameter of the nozzle diameter.

In another particular embodiment of the above described methods, the concentration of the hydrogel polymer in the emulsion is below 3%.

In further embodiments of the methods of the present invention, the concentration of the hydrogel polymer in the emulsion is between 0.5 to 1.5% and the nozzle has a diameter between 10 and 40 μm.

In particular embodiments of all of the methods of the present invention, the bioactive agent is hydrophobic.

In other embodiments of the methods of the present invention, the bioactive agent is a hydrophilic bioactive agent and the method step (a) described above, comprises the step of preparing a water-in-oil emulsion of an aqueous solution of the hydrophilic bioactive agent and a solution of a polymer.

In particular embodiments of the methods of the present invention, the microparticles have a size ranging between 10 and 20 μm.

In particular embodiments of the methods of the present invention, the polymer is a poly(ethylene oxide)terephthalate and poly(1,4-butylene)terephthalate (PEGT/PBT) copolymer.

In particular embodiments of the methods of the present invention wherein an inclined surface is used, the length and slope of the inclined surface is configured such that a particle ejected from the nozzle moves along the inclined surface for a time period between 2 to 60 seconds.

In further particular embodiments of the methods of the present invention, the methods comprise, following step (c), an additional step (d), wherein the particles are further hardened by stirring.

In particular embodiments of the methods of the present invention, the nozzle has a diameter smaller than 30 μm.

In particular embodiments of the methods of the present invention, the polymer is a hydrogel polymer and the method is performed in the absence of stabilizer in the receiving fluid.

Another aspect of the present invention provides populations of monodisperse polymer microparticles with a size between 1 and 100 μm and more particularly between 1 and 50 μm, these particles comprising one or more bioactive agents. These populations are obtainable by the methods described above.

In particular embodiments of the populations of monodisperse polymer microparticles of the invention, the polymer is a hydrogel polymer, and more than 90% of the microparticles have a diameter within 0.5 μm of the average value of the population.

In particular embodiments of the populations of monodisperse polymer microparticles, the hydrogel polymer is a PEGT/PBT copolymer.

In alternative embodiments of the populations of monodisperse polymer microparticles provided by the invention, the polymer comprises a PLA-PEO polymer (Polylactic acid-polyethylene oxide), and more than 90% of the microparticles has a diameter within 0.7 μm of the average value of said population.

In further particular embodiments of the populations of monodisperse polymer microparticles of the invention, more than 90% of the particles are within 4% of the number averaged diameter.

In particular embodiments of the populations of monodisperse polymer microparticles provided by the invention, these microparticles comprise a hydrophilic bioactive agent or comprise a hydrophobic bioactive agent.

The present invention also includes the use of the monodisperse microparticle populations as detailed above for drug delivery. The present invention also provides a pharmaceutical composition comprising the monodisperse microparticle populations as detailed above.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference Figures quoted below refer to the attached drawings.

Figure 1:
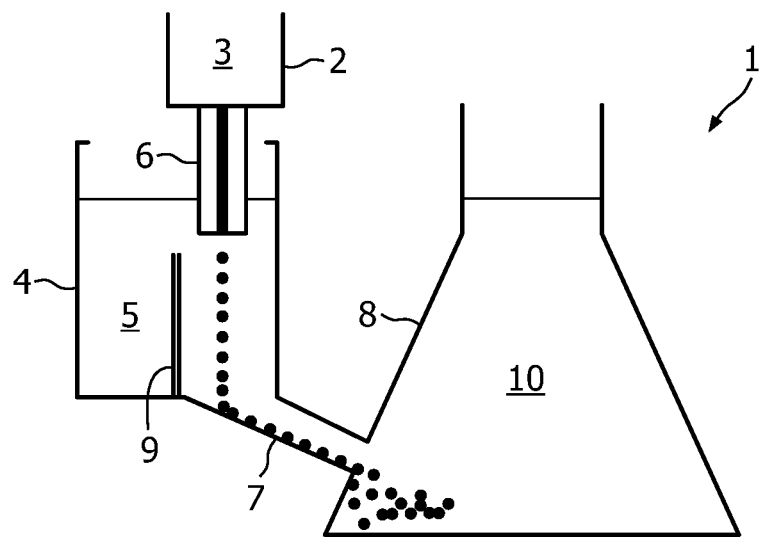
FIG. 1 shows a schematic representation of a device (1) suitable for use in the method according to the invention, comprising a first reservoir (2), a second reservoir (4) comprising or connected to an inclined surface (7) connected to a collection bath (8). The device further comprises a nozzle (6) which is configured such that the emulsion droplets when extruded from the nozzle (6) land on the inclined surface (7), sliding/rolling down the surface until they have reached the collection bath. In the methods of the invention, an emulsion (3) introduced into the first recipient (2) is injected using a nozzle (2) into a second recipient (4) into a receiving fluid (5). Optionally, a vertical wall (9) in the second recipient (4) allows for shifting the nozzle first to a position in/above a first compartment to set frequency, pulse amplitude and pressure without the droplets reaching the collection bath (8). When the parameters are set, the nozzle can be shifted, while keeping it submerged, to a position in/above the second compartment, which is connected to/comprises the inclined surface (7). In particular embodiments of the methods of the invention, the emulsion droplets ejected from the nozzle (6) fall onto an inclined surface (7), on which they slide for about 2 seconds before reaching the collection bath (8) filled with fluid (10). Emulsion droplets sliding down on the inclined surface are illustrated.

In the different Figures, the same reference signs refer to the same or analogous elements.

DETAILED DESCRIPTION OF THE EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

The term "microparticle" as used herein refers to a particle with a diameter between 1 and 100 μm.

The term "bioactive agent" generally refers to any physiologically or pharmacologically active substance or a substance suitable for detection within or withdrawn from a biological of physiological environment.

The term "hydrophilic" is used herein as a synonym for "water soluble" and is used herein to describe tendency to attract water molecules and increased water solubility. A bioactive agent is considered to be water soluble if 0.2 grams or more of the agent can be dissolved per liter water (=0.2 mg/ml) at 25° C. under atmospheric pressure. The term "monodisperse" as used herein when referring to a plurality of microparticles indicates that the standard deviation of the size distribution is less than 10%.

The term "hydrogel" as used herein refers to a network of natural or synthetic polymer chains in which the network swells upon contact with water to a point where the physicochemical properties of the polymer chains prevent further swelling due to covalent or non-covalent binding domains within the network. Depending on the amount of hydratable groups in the polymer, dehydrated hydrogels swell in volume upon hydration with a factor 3 to 10, typically with a factor between about 3 and about 4 (referred to herein as the hydration degree).

The present invention provides new and improved microparticles suitable for drug delivery and methods for producing them.

One aspect of the present invention provides methods for preparing a plurality of monodisperse polymer microparticles comprising one or more bioactive agents. More particularly, the microparticles have an average size of 1 to 100 μm, more particularly between 2-50 μm, most particularly between 15-30 μm. In more particular embodiments the microparticles have an average size of 10 to 20 μm.

According to the methods of the present invention the polymer microparticles comprising hydrophilic bioactive agents are formed using inkjetting technique. A disadvantages of known methods of inkjetting, such as described in U.S. Pat. No. 6,669,961 is the fragility of the inkjetted emulsion droplets. Stirring during solvent extraction has to occur very gently, otherwise the droplets break-up easily.

According to the present invention, an inkjetting technique is used whereby the polymer microparticles are hardened by allowing the microparticles to drop within a liquid (receiving fluid). The receiving fluid is an aqueous solution which can be buffered and can contain additional compounds such as salts, surfactants stabilisers, organic compounds up to 2, 10 or 20%, or other additives. During this initial swelling and/or hardening the receiving fluid is typically not stirred to avoid mechanical damaging, caused for example by collision of the particles with each other. By choosing the appropriate height of the recipient, it can be ensured that the emulsion droplets fall a specific distance by gravity thereby hardening to a certain extent, after which they are removed from the recipient and can be stirred for further hardening.

According to one aspect of the present invention methods and devices for inkjetting of microparticles are provided whereby emulsion droplets ejected from a nozzle are contacted within the receiving fluid with a downwardly inclined surface and start swelling and/or hardening while rolling down or sliding on this surface. Most particularly, the inclined surface has a gradually changing slope. Indeed, it has been found that, by allowing the emulsion droplets to roll or slide down a gradually changing slope within the receiving fluid, instead of falling under gravity, they age within the receiving fluid for a specified period of time and monodisperse particles can be obtained with increased uniformity.

The length of the inclined surface can vary and will be determined, inter alia, by the size of the droplets. Equally the structure of the slope and the material used for the slope can influence the behaviour of the swelling and/or hardening particles, for instance the roughness and hydrophobicity of its material has an effect and can be adjusted by the skilled person to further control the time required for the droplets to move down the inclined surface. In particular embodiments the length of the surface and its inclination is designed to ensure a gradual de-acceleration of the emulsion droplets such that the movement by rolling or sliding of the emulsion droplets along the slope takes between about 2 and 60 seconds. In particular embodiments, conditions are chosen wherein the movement of the particles along the slope takes less than 10 or even less than 5 seconds. In particular embodiments, the length of the inclined surface is envisaged to be between 1 cm and 2 cm, or more.

In particular embodiments, the slope of the inclined surface is fixed. More particularly, the slope of the surface is between 10 and 45 degrees, between 10 and 30 degrees, or between 20 and −40 degrees. The inclined surface can be linear, for example a straight tube. Typically the inclined surface extends from a position under the nozzle (allowing the droplets to be contacted with or drop onto the inclined surface) to a second recipient for collection and optionally further processing of the obtained microparticles. The distance between the opining of the nozzle and the inclined surface (or the time needed for the droplets to reach the inclined surface from the nozzle) is included within the optimal hardening/swelling distances (swelling times) envisaged for the methods of the present invention. The inclined surface can be completely or in part positioned within the recipient in which the ejection nozzle is submerged or can be linked thereto in such a way that, at least in particular positions of the nozzle, emulsion droplets ejected from the nozzle are automatically (e.g. as a result of gravity or by a direct connection between nozzle and inclined surface) contacted with the inclined surface.

In particular embodiments, an inclined surface having a gradually changing slope is envisaged. Particularly it is envisaged that while gradually changing the slope maintains an inclination of at least 10 degrees, more particularly at least 20° at each point of the slope. Typically, the slope of the inclined surface gradually changes from 90° (corresponding to a vertical drop from the nozzle) to at least 10°, more particularly at least 20° at the end of the inclined surface (where the microparticles are collected, e.g. in a collection bath (8)).

In particular embodiments, more particularly where a surface of an extended length is envisaged, the inclined surface is curved or spiralled to create the required length in a small volume.

The inclined surface can be flat or can comprise curved edges to prevent the droplets from falling off the surface. In particular embodiments, the surface is a groove or a tube which connects to a collection bath (8) which containing a fluid (10) such as the receiving fluid.

After rolling or sliding down the inclined surface, the emulsion droplets are sufficiently hardened/swollen and can optionally be further processed by regular stirring. Accordingly, the droplets can be collected in a collection bath (8). Additionally or alternatively, droplets can be taken out of the receiving fluid and recovered.

The passive processing step of the present invention has the advantage of circumventing damage to jetted droplets and is in particular embodiments carried out in the absence of additives such as polyvinylalcohol typically used to stabilize the emulsion droplets or formed microparticles.

The methods and tools of the present invention are of particular interest in the generation of microparticles for delivery of bioactive agents and thus optionally comprise one or more bioactive agents.

According to one embodiment of the invention the tools and methods of the present invention are used for the generation of microparticles comprising hydrophobic bioactive agents. According to this embodiment hydrophobic bioactive agents are mixed together with a polymer into an organic solvent to prepare an emulsion, which is then inkjetted according to the methods of the present invention. Methods of preparing emulsions of polymers and hydrophobic agents are well known to the skilled person.

According to another embodiment of the present invention, the methods and tools of the present invention are used for the generation of microparticles comprising hydrophilic or water-soluble bioactive agents. Polymer microparticles comprising hydrophilic bioactive agents are formed using the double emulsification technique. In a first step, the hydrophilic bioactive agent is dissolved in an aqueous solution and mixed with a solution of the encapsulating polymer in a first solvent, which is immiscible with water or has a limited solubility in water (less than 5 or 2%), such as dichloromethane which has a solubility in water of 1.3%, to form a primary water-in-oil emulsion. The primary emulsion is added to an aqueous second solvent to form a secondary emulsion and homogenization is continued. The first and second solvents are selected such that the first solvent is immiscible or partly miscible with the second aqueous solvent, but the polymer is immiscible with the second solvent. After introduction of the water-in-oil emulsion, the first solvent will migrate into the second solvent. In this way polymer microparticles are obtained which contain multiple crevices comprising the water-soluble bioactive agent. This is followed by solvent evaporation or extraction. According to the present invention, tools and methods are provided whereby microparticles of increased homogeneity can be obtained. In the methods and tools of the invention the microparticles in the aqueous phase are dropped from a nozzle (1) onto an inclined surface (6) within an aqueous receiving fluid (4). More particularly, the inclined slope has a gradually changing slope, as described above.

Accordingly, the methods of the present invention are envisaged for the production of microparticles comprising either hydrophilic or hydrophobic bioactive agents. Nucleic acids, carbohydrates and, in general, proteins and peptides are water soluble or hydrophilic and are generally optimally incorporated into microparticles using the double emulsion technique, as described above. However, hydrophobic drugs, including some peptides (e.g. when a large proportion of the amino acids in a peptide carry hydrophobic side chains) can be dissolved together with the polymer in the organic solvent directly to prepare an emulsion for inkjetting according to the methods of the present invention. Accordingly, the present invention includes a pharmaceutical composition including the microparticles obtainable by the present invention.

Although, in view of the delicacy of proteins and peptides, the present methods and tools are particularly useful for making polymers loaded with proteins and peptides, it is of course also envisaged to load a polymer with a substance other than a protein or peptide. For instance, bioactive agents which are small molecules, lipids, lipopolysaccharides, polynucleotides and antisense nucleotides (gene therapy agents) are also envisaged. Such biologically active agents, which may be incorporated thus include non-peptide, non-protein drugs. It is possible within the scope of the present invention to incorporate drugs of a polymeric nature, but also to incorporate drugs of a relatively small molecular weight of less than 1500, or even less than 500.

Accordingly, compounds envisaged for use as bioactive agents in the context of the present invention include any compound with therapeutic or prophylactic effects. It can be a compound that affects or participates in tissue growth, cell growth, cell differentiation, a compound that is able to invoke a biological action such as an immune response, or a compound that can play any other role in one or more biological processes. A non-limiting list of examples includes antimicrobial agents (including antibacterial, antiviral agents and anti-fungal agents), anti-viral agents, anti-tumor agents, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, anti metabolites, antiproliferatives (including anti-angiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, ACE inhibitors, free radical scavengers, chelators, antioxidants, anti polymerases, and photodynamic therapy agents.

As indicated above particular group of compounds that can be used for loading a polymer according to the invention is formed by peptides and proteins, of which in principle any kind may be incorporated according to the present invention. Relatively small peptides may be referred to by the number of amino acids (e.g. di-, tri-, tetrapeptides). A peptide with a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterised by the so called quaternary structure, a conglomerate of a number of polypeptides that are not necessarily chemically linked by amide bonds but are bonded by forces generally known to the skilled professional, such as electrostatic forces and Vanderwaals forces. The term peptides, proteins or mixtures thereof as used herein is to include all above mentioned possibilities.

Usually, the protein and/or peptide are selected on the basis of its biological activity. Depending on the type of polymer chosen, the product obtainable by the present process is highly suitable for controlled release of proteins and peptides. In a particular embodiment, the protein or peptide is a growth factor.

Other examples of peptides or proteins or entities comprising peptides or proteins which may advantageously be contained in the loaded polymer include, but are not limited to, immunogenic peptides or immunogenic proteins, which include, but are not limited to, the following:

Toxins such as diphtheria toxin and tetanus toxin.

Viral surface antigens or parts of viruses such as adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus.

Bacterial surface antigens or parts of bacteria such as *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera* and *Yersinia pestis*.

Surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), *Stronglyloides duodenale* (hookworm), *Ancyclostoma duodenale* (hookworm), *Necator americanus* (hookworm), *Wucheria bancrofti* (filariasis), *Brugia malaya* (filariasis), *Loa loa* (filariasis), *Dipetalonema perstaris* (filariasis), *Dracuncula medinensis* (filariasis), and *Onchocerca volvulus* (filariasis).

Immunoglobulins such as IgG, IgA, IgM, Antirabies immunoglobulin, and Antivaccinia immunoglobulin.

Antitoxin such as Botulinum antitoxin, diphtheria antitoxin, gas gangrene antitoxin, tetanus antitoxin.

Antigens which elicit an immune response against foot and mouth disease.

Hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

Examples of other proteins or peptides are albumin, atrial natriuretic factor, renin, superoxide dismutase, alpha 1-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH and metkephamid.

Anti-tumor agents such as altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin and paclitaxel.

Antimicrobial agents comprising:

Antibiotics such as ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, and cephalexin. Aminoglycosides such as amikacin, neomycin, dibekacyn, kanamycin, gentamycin, netilmycin, kanamycin, tobramycin. Macrolides such as amphotericin B, novobiocin, bacitracin, nystatin, clindamycin, polymyxins, colistin, rovamycin, erythromycin, spectinomycin, lincomycin, vancomycin Tetracyclines such as chlortetracycline, oxytetracycline, demeclocycline, rolitetracycline, doxycycline, tetracycline and minocycline. Other antibiotics such as chloramphenicol, rifamycin, rifampicin and thiamphenicol.

Chemotherapeutic agents such as the sulfonamides sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole and trimethoprim with sulfamethoxazole or sulfametrole.

Urinary tract antiseptics such as methanamine, quinolones (norfloxacin, cinoxacin), nalidixic acid, nitro-compounds (nitrofurantoine, nifurtoinol) and oxolinic acid.

Drug for anaerobic infections such as metronidazole.

Drugs for tuberculosis such as aminosalicyclic acid, isoniazide, cycloserine, rifampicine, ethambutol, tiocarlide, ethionamide and viomycin.

Drugs for leprosy such as amithiozone, rifampicine, clofazimine, sodium sulfoxone and diaminodiphenylsulfone (DDS, dapsone).

Antifungal agents such as amphotericin B, ketoconazole, clotrimazole, miconazole, econazole, natamycin, flucytosine, nystatine and griseofulvin.

Antiviral agents such as aciclovir, idoxuridine, amantidine, methisazone, cytarabine, vidarabine and ganciclovir.

Chemotherapy of amebiasis such as chloroquine, iodoquinol, clioquinol, metronidazole, dehydroemetine, paromomycin, diloxanide, furoatetimidazole and emetine.

Anti-malarial agents such as chloroquine, pyrimethamine, hydroxychloroquine, quinine, mefloquine, sulfadoxine/pyrimethamine, pentamidine, sodium suramin, primaquine, trimethoprim and proguanil.

Anti-helminthiasis agents such as antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Anti-inflammatory agents such as acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen and tolmetin.

Anti-gout agents such as colchicine and allopurinol.

Centrally acting (opoid) analgesics such as alfentanil, methadone, bezitramide, morphine, buprenorfine, nicomorphine, butorfanol, pentazocine, codeine, pethidine, dextromoramide, piritranide, dextropropoxyphene, sufentanil and fentanyl.

Local anesthetics such as articaine, mepivacaine, bupivacaine, prilocalne, etidocaine, procaine, lidocaine and tetracaine.

Drugs for Parkinson's disease such as amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide and trihexyphenidyl.

Centrally active muscle relaxants such as baclofen, carisoprodol, chlormezanone, chlorzoxazone, cyclobenzaprine, dantrolene, diazepam, febarbamate, mefenoxalone, mephenesin, metoxalone, methocarbamol and tolperisone.

Corticosteroids comprising:

Mineralocorticosteroids such as cortisol, desoxycorticosterone and fluorohydrocortisone.

Glucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide).

Androgens comprising:

Androgenic steroids used in therapy such as danazole, fluoxymesterone, mesterolone, methyltestosterone, testosterone and salts thereof.

Anabolic steroids used in therapy such as calusterone, nandrolone and salts thereof, dromostanolone, oxandrolone, ethylestrenol, oxymetholone, methandriol, stanozolol methandrostenolone and testolactone.

Antiandrogens such as cyproterone acetate.

Estrogens comprising sstrogenic steroids used in therapy such as diethylstilbestrol, estradiol, estriol, ethinylestradiol, mestranol and quinestrol.

Anti-estrogens such as chlorotrianisene, clomiphene, ethamoxytriphetol, nafoxidine and tamoxifen.

Progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

Thyroid drugs comprising:

Thyroid drugs used in therapy such as levothyronine and liothyronine Anti-thyroid drugs used in therapy such as carbimazole, methimazole, methylthiouracil and propylthiouracil.

According to a particular embodiment, the bioactive agent is a marker substance, such as a contrast agent or a label. Preferably the contrast agent or label is hydrophobic, or of a particulate nature. These types of agents can be incorporated very efficiently and will not release from the polymer matrix until it has degraded to a large extent. Particularly suited agents are iodinated X-ray contrast agents in the form of an liquid. For this purpose the product Ethiodol can for instance be used, which is a iodinated poppyseed oil. For higher iodine loadings iodinated oils can be synthesized, for instance octan-2-yl 2,3,5-triiodobenzoate, which has a iodine content of more than 1000 mg/ml.

The polymer microparticles can comprise one or more bioactive agents or can comprise a combination of a therapeutic and a contrast agent. Apart from bioactive agents which are water soluble, other water-soluble compounds can be incorporated such as anti-oxidants, ions, chelating agents, dyes, imaging compounds. Also, in addition to hydrophobic bioactive compounds other compounds may be added to the solvent which is used for dissolving the polymer. These hydrophobic compounds can be anti-oxidants, ions, chelating agents, dyes, or imaging compounds. As indicated above, the methods and tools of the present invention can be used to generate both hydrophobic and hydrophilic agent-containing polymer microparticles. Hydrophobic agents are incorporated directly into the polymer solution and hydrophilic agents are incorporated via the double emulsion technique.

For the methods according to this aspect of the invention, any type of biocompatible polymer can be used. In certain embodiments the biocompatible polymer is also biodegradable. Examples of biodegradable biocompatible polymers are poly(lactides), poly(glycolides), poly(lactide-co-glycolides), polycaprolactone, polycarbonates, polyesteramides, polyanhydrides, poly(amino acids), polyorthoesters, poly(dioxanones), poly(alkylene alkylate)s, polyacetals, polycyanoacrylates, biodegradable polyurethanes, blends and copolymers thereof. Typically polymers comprising poly(lactides), copolymers of lactides and glycolides, blends thereof, or mixtures thereof are used. Such polymers can be formed from monomers of a single isomeric type or a mixture of isomers.

Examples of non-biodegradable biocompatible polymers are polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide (PEO), blends and copolymers thereof.

In a particular embodiment, the polymer is a PLA-PEO (polylactic acid-polyethylene oxide) copolymer.

Another aspect of the present invention relates to methods and tools for preparing monodisperse polymer microparticles with a size of between 1 and 100 μm, more particularly between 2 and 50 μm, comprising a bioactive agent, using inkjetting, wherein the polymer is a hydrogel. It has been found that the use of hydrogel polymers allows the generation of particles of less than 30 μm from a low concentration of polymer, which was a problem with previously disclosed techniques (e.g. U.S. Pat. No. 6,669,961). Upon swelling and/or hardening of an inkjetted polymer particle in a liquid, the organic solvent diffuses out of the particle, while there is a counter-diffusion of water into the microparticle. The advantageous consequences of this counter diffusion in the formation of hydrogel particles have not yet been appreciated. After injection of a hydrogel droplet into an aqueous receiving fluid, a large amount of water is absorbed by the hydrogel particle leading to a significant swelling. This swelling is independent of the time that the droplets are in contact with the aqueous receiving fluid. An equilibrium value is almost instantaneously obtained. Upon leaving a nozzle, a droplet has a diameter slightly larger that the diameter of the nozzle, depending on the applied pressure and the amount of jetted polymer. In practice jetting from nozzles with a diameter of e.g. 30 micron generates droplets with a diameter of about 45 μm. The final diameter of a hydrogel particle will depend on the combination of polymer concentration and degree of hydration of a hydrogel which is determined by the number of hydratable groups on the polymer. The compensating swelling in volume of a dehydrated hydrogel particle by water is generally a factor 3 to 4, but can go up to a value of 5, 6, 8 or 10.

Generally, as a result of the removal of the solvent, a jetted hydrogel droplet with a diameter of 50 μm with a polymer concentration of 1 to 3%, first shrinks in volume with a factor 100 to 33, and in diameter to a particle with a diameter of about 11 to 16 μm. Such particles when hydrated and increasing in volume with a factor 3, swell to particles with a diameter of about 15 to 22 μm. Particles, which when hydrated increases in volume with a factor 4, swell to particles with a diameter of respectively about 17 and 25 μm. It is within the ambit of the skilled person to select a type of polymer (i.e. hydratation degree) and polymer concentration in accordance with the desired size for the resulting hydrated hydrogel polymer particle.

The hydrogel polymers thus have the advantage that polymer droplets with a relatively small volume can be jetted while obtaining relatively large microparticles after swelling. By using smaller droplets, the diffusion of the solvent present in the hydrogel out of the droplet is markedly increased. As a consequence, the total time needed for the swelling and/or hardening of the polymer particle is dramatically decreased. Moreover, as the receiving fluid is less contaminated with solvent, a steeper gradient of solvent between the particle and the receiving fluid is maintained again promoting the swelling and/or hardening of the polymer particle.

Accordingly, in particular embodiments of the invention, the use of emulsions with a low concentration of hydrogel polymer, for example 0.5 to 3%, more particularly 0.5 to 2% such as 1.5% of hydrogel polymer in the emulsion is envisaged. In further particular embodiments such emulsions are jetted from nozzles having a diameter of between 1 and 100 μm, more particularly between 10 and 50 μm, even more particularly between 20 and 30 μm. The controlled swelling of inkjetted droplets of hydrogel emulsions, by adjusting the nozzle diameter allows the generation of microparticles having a diameter of between 40 and 120% of the nozzle diameter, more particularly having a diameter of more than 70 to 85% (in particular more than 75%, more than 80%, or more than 85%) of the diameter of the nozzle used for inkjetting. In particular embodiments the diameter of the hydrogel particle obtained after swelling can be as large or larger that the diameter of the nozzle.

The Examples section demonstrates that hydrogel polymer concentrations of about 1% jetted from a nozzle with a diameter of 20 μm can be used to obtain polymer particles with a diameter of about 17 μm, corresponding to 85% of the nozzle diameter.

As indicated above, the use of hydrogel forming polymers for the manufacture of microparticles allows the use emulsions with a polymer concentration below 3%, or even below 2%, which is significantly lower than the polymer concentrations traditionally used. Such emulsions have a lower viscosity which facilitates inkjetting because less pressure is needed to force the emulsion through the inkjetting device. The use of hydrogel forming polymers in addition has the advantage that during ink-jetting, nozzle contamination is decreased.

The invention thus provides methods for producing hydrogel polymer microparticles with a size ranging between 1 and 50 μm comprising a bioactive agent. Typically, the methods of the invention comprise the step of preparing an emulsion of a hydrogel forming polymer as described above, comprising a bioactive agent, and ejecting droplets of the emulsion from a nozzle submerged in an aqueous receiving fluid using an assistant pressure and applying a frequency. The droplets are hardened into microparticles by allowing the droplets to move within the receiving fluid for a time period which ensures removal of solvent and saturation with water of said droplets. Typically, more than 30%, particularly more than 40%, more particularly more than 50%, most particularly between 60 and 98% or more of the solvent is removed and replaced all or in part by water. In particular embodiments of the methods of the invention, the particles are moved in the receiving fluid without agitation. Most particularly the particles are moved in the receiving fluid by allowing them to slide on an inclined surface as described herein.

Accordingly, the present invention provides for monodisperse populations of hydrogel polymer particles, having a diameter between 1 and 100 μm, more particularly with a diameter ranging between 10 and 30 μm, most particularly between 10 and 20 μm. Particles with a size between 10 and 20 μm are particularly suitable for medical applications such as the creation of emboli in the smallest blood vessels.

According to a particular embodiment, the hydrogel polymer microparticles comprise one or more bioactive agents. In particular embodiments, the hydrogel particles comprise a hydrophilic bioactive agent. Alternatively, the bioactive agent is hydrophobic and a double emulsion technique is used as described above. The nature of the bioactive agent is not critical and suitable examples of bioactive agents envisaged are disclosed hereinabove.

According to a further particular embodiment, the hydrogel microparticles are produced by inkjetting into a solvent whereby the microparticles are dropped onto an inclined surface, having a gradually changing slope, as described above.

Hydrogels are particularly useful for controlled delivery, especially of hydrophilic materials, since the water soluble regions of the polymer enable access of water to the materials entrapped within the polymer. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. Degradation of the polymer facilitates eventual controlled release of free macromolecules in vivo by gradual hydrolysis of the terminal ester linkages. Generally, a hydrogel is formed from a biodegradable, polymerizable, macromer including a core, an extension on each end of the core, and an end cap on each extension. The core is a hydrophilic polymer or oligomer; each extension is a biodegradable oligomer; and each end cap is an oligomer, dimer or monomer capable of cross-linking the macromers. In another particular embodiment, the core includes hydrophilic poly(ethylene glycol) oligomers of molecular weight between about 400 and 30,000 Da; each extension includes biodegradable poly(α-hydroxy acid) oligomers of molecular weight between about 200 and 1200 Da; and each end cap includes an acrylate-type monomer or oligomer (i.e., containing carbon-carbon double bonds) of molecular weight between about 50 and 200 Da which are capable of cross-linking and polymerization between copolymers. Another embodiment incorporates a core consisting of poly(ethylene glycol) oligomers of molecular weight about 10,000 Da; extensions consisting of poly(glycolic acid) oligomers of molecular weight about 250 Da; and end caps consisting acrylate moieties of about 100 Da molecular weight.

Examples of suitable materials for use as the core water soluble region are poly(ethylene glycol), poly(ethylene oxide), poly(vinyl alcohol), poly(vinylpyrrolidone), poly (ethyloxazoline), poly(ethylene oxide)-co-poly(propyleneoxide) block copolymers, polysaccharides or carbohydrates such as hyaluronic acid, dextran, heparin sulfate, chondroitin sulfate, heparin, or alginate, or proteins such as gelatin, collagen, albumin, or ovalbumin.

Biodegradable regions can be constructed from polymers or monomers using linkages susceptible to biodegradation, such as ester, peptide, anhydride, orthoester, and phosphoester bonds.

Examples of biodegradable components which are hydrolyzable are polymers and oligomers of glycolide, lactide, ϵ-caprolactone, other α-hydroxy acids, and other biologically degradable polymers that yield materials that are non-toxic or present as normal metabolites in the body. Suitable poly(α-hydroxy acid)s are poly(glycolic acid), poly(DL-lactic acid) and poly(L-lactic acid). Other useful materials include poly (amino acids), poly(anhydrides), poly(orthoesters), and poly (phosphoesters). Polylactones such as poly(ϵ-caprolactone), poly(ϵ(3 caprolactone), poly(δ-valerolactone) and poly(γ-butyrolactone), are also useful.

Examples hereof are PEG-oligolactyl-acrylates. Herein, poly(ethyleneglycol) or a PEG central structural unit (core) is useful on the basis of its high hydrophilicity and water solubility, accompanied by excellent biocompatibility. A short poly(alpha-hydroxy acid), such as polyglycolic acid, is a suitable chain extension because it rapidly degrades by hydrolysis of the ester linkage into glycolic acid, a harmless metabolite. Such networks can be used to entrap and homogeneously disperse water-soluble drugs and enzymes and to deliver them at a controlled rate. Other suitable chain extensions are polylactic acid, polycaprolactone, polyorthoesters, and polyanhydrides. Polypeptides may also be used.

In a particular embodiment the hydrogel microparticles are prepared from a copolymer of a polyalkylene glycol and an aromatic polyester. This copolymer comprises from about 30 wt. % to about 99 wt. %, especially 30 to 90 wt. %, based upon the weight of the copolymer, of a first component which comprises a polyalkylene glycol and has units of the formula —OLO—CO-Q-CO—, wherein L is a divalent organic radical remaining after removal of terminal hydroxyl groups from a poly(oxyalkylene)glycol, and Q is a divalent organic radical, and from about 1 wt. % to about 70 wt. %, especially 10 to 70 wt. %, based on the weight of the copolymer, of a second component which is an aromatic polyester, having units of the formula —O-E-O—CO—R—CO— wherein E is a substituted or unsubstituted alkylene or oxydialkylene radical having from 2 to 8 carbon atoms, and R is a substituted or unsubstituted divalent aromatic radical.

The polyalkylene glycol, in one embodiment, is selected from polyethylene glycol, polypropylene glycol, and polybutylene glycol and copolymers thereof such as poloxamers. In one embodiment, the polyalkylene glycol is polyethylene glycol. The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-butylene (tetramethylene) and similarly for higher alkylene homologues. The polyalkylene glycol component is terminated with a dicarboxylic acid residue —CO-Q-CO— if necessary to provide a coupling to the polyester component. The group Q may be an aromatic group having the same definition as R, or may be an aliphatic group such as ethylene, propylene, butylene and the like.

In the polyester component, the divalent aromatic group R may be phenylene, pyridylene, naphthylene, biphenyl, oxydiphenyl, sulphodiphenyl, methylenediphenyl, optionally substituted by up to four, particularly up to two substituents selected from chloro, nitro, and C1-C4 alkoxy and further fluoro, hydroxy and C1-C4 alkyl. Typically, the aromatic radical R is unsubstituted, and particularly, R is 1,4-phenylene. Examples of the polyester —O-E-O—CO—R—CO— comprise poly(ethylene terephthalate), poly(propylene terephthalate), poly(butylene terephthalate), poly(butylene isophthalate), poly(ethylene 4,4'-methylenediphenyldicarboxylate), poly(butylene 5,6,7,8-tetrahydronaphthalene-1,4-dicarboxylate) and the like.

In a particular embodiment, the polyester is selected from polyethylene terephthalate, polypropylene terephthalate, and polybutylene terephthalate. More particularly, the polyester is polybutylene terephthalate. In a very particular embodiment, the copolymer is a polyethylene glycol/polybutylene terephthalate block copolymer.

The polyalkylene glycol may have a molecular weight of from about 200 to about 20,000. The exact molecular weight of the poly(oxyethylene)glycol is dependent upon a variety of factors, including the type of biologically active agent encapsulated by the matrix.

In a particular embodiment the hydrogel polymer is a copolymer of poly(ethylene oxide) terephthalate and poly(1,4-butylene)terephthalate (PEGT/PBT). Wherein PEGT/PBT weight ratios can range from 80/20 over 70/30 to 60/40. In particular embodiments, the polyethylene glycol component of the 70/30 and 60/40 copolymers have a molecular weight of 1,000. In other particular embodiments the 80/20 copolymers, have a polyethylene glycol components with respectively molecular weights of 1,000, 2,000, and 4,000.

The methods of the present invention wherein hydrogel forming polymers are used in inkjetting have the additional advantage that stabilizing additives are not needed. Generally in the preparation of microparticles of biodegradable polymers additives are needed. The most common additive used is polyvinyl alcohol (PVA), which is commercially available in different molecular weights and degrees of hydrolysis. PVA has three functions in preparing microparticles from mixing solutions of biodegradable polymers in an organic solvent with water. First PVA is an excellent stabiliser for the emulsion droplets that are formed after inkjetting. Secondly PVA acts as a stabiliser for the hardened microparticles and thirdly PVA has an influence on the shear forces between emulsion droplets.

The use of a hydrogel-forming polymer in particular embodiments of the present invention, removes the need for the stabilising action of PVA on emulsion droplet stability and microparticle stability. Similarly, a viscosity-enhancing agent is no longer needed to control the microparticle size. With submerged jetting and controlled swelling in an aqueous solution according to the present invention, breaking up of emulsion droplets using shear forces does not take place and, therefore the process can take place in the absence of added PVA to the continuous phase. Therefore less washing steps are needed and the subsequent faster processing likely leads to more efficient encapsulation.

The methods of the present invention further allow the use of double emulsion technique wherein a surfactant such as Pluronics can be omitted from the first emulsion step when hydrogel polymers are used.

In the inkjetting methods and tools of the present invention, a bioactive agent in polymer emulsion is introduced into a fluid (also referred to as receiving fluid) with an assistant pressure using a nozzle in combination with a piezo-electric device such as an inkjet head. The nozzle is submerged into the receiving fluid according to known methods of submerged inkjetting.

Devices for submerged inkjetting of microparticles are described in e.g. WO2006003581 and U.S. Pat. No. 6,599,627.

Such devices typically comprise:
a first reservoir (2) for holding the emulsion (3) of the bioactive agent and the polymer,
a second reservoir (4) for holding the receiving fluid (5), and
a jetting module having at least one nozzle (6) for jetting the emulsion into the receiving fluid.

In the devices of the present invention, the second reservoir (4) for receiving fluid and the nozzle (6) are placed such that the nozzle (6) is submerged into the receiving fluid, upon filling up the second reservoir (4) with receiving fluid.

The diameter of the nozzle can be adjusted depending on the size of the particle to be obtained and/or the concentration of the polymer used, and is typically between 1-100 μm. In particular embodiments, the devices of the present invention comprise a nozzle with a diameter of between 20 and 50 μm.

In one embodiment, the device comprises a control system to control the jetting at a jetting rate in the range of 100 kHz$^{-1}$ to 0.1 kHz$^{-1}$. In another embodiment the control system is arranged to operate the jetting in a pulsed fashion, in particular the control system being arranged to apply block form excitation pulses to the jetting module. In another embodiment the jetting system includes several nozzles and the control system is arranged to adjust the droplet-sizes for the individual nozzles. In another embodiment the reservoir is provided with a temperature control system.

A particular embodiment of submerged inkjetting applicable in the methods of the present invention is described in Böhmer et al. (2006) (cited above). Herein experiment are conducted using piezo-driven Microdrop ink-jet nozzles (MK-140H) with diameters of 50, 30 and 20 μm. An external pulse generator is used (Fluke PM5139) to obtain frequencies in the range of 20 kHz. An optional Microdrop driver (MD-E-201H) also allows for taking pulse-triggered images, to follow the drop formation process. The nozzle is placed in the liquid of a reservoir. A constant pressure is applied to prevent blockage of the nozzle and allow for a high droplet formation rate because the static fluid pressure of the ink-reservoir was not sufficient. Typical pressures are 0.3 bar for a 50 μm nozzle, 0.8 bar for a 30 μm nozzle and 1.6 bar for a 20 μm nozzle. In one embodiment (illustrated in FIG. 1) the reservoir contains two compartments, separated by a vertical wall (9'), whereby one compartment is used to set the frequency and the pressure, so as to obtain a well-defined array of emulsion droplets. When this is achieved, the nozzle is placed in the second compartment, while keeping it jetting and submerged, which is the compartment for production of the emulsion. After 15 min the nozzle is shifted back, and the pulse generator is turned off. The nozzle is removed from the solution, while the pressure is still applied. Only after the nozzle is in full air, the assistance pressure is turned off. This is done to ensure that no aqueous solution flows back into the nozzle, which can cause clogging. With an inkjetting device, such as described above, droplets are jetted at a rate of about 5000 to 100.000 droplets/second. Typically the production rate is about 25.000 per second.

Figure 2:
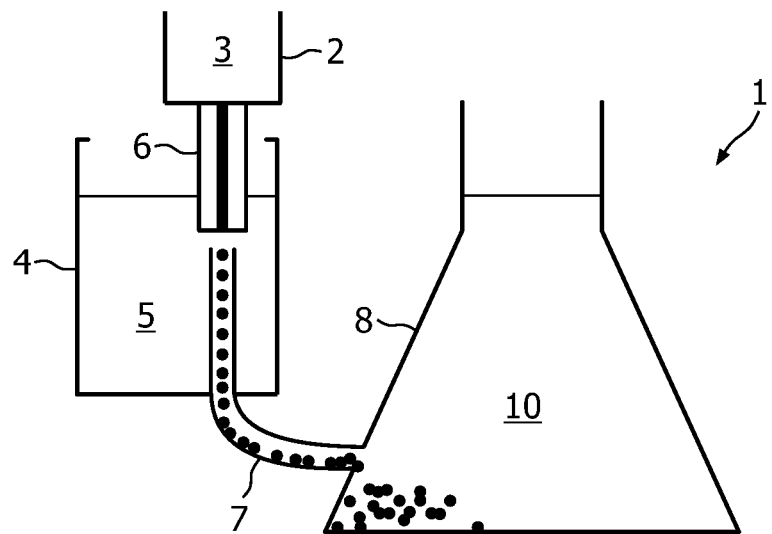
FIG. 2 shows a schematic representation of a particular embodiment of such a device (1), comprising a first reservoir (2), a second reservoir (4) comprising or connected to an inclined surface (7) having a gradually changing slope (e.g. in the form of a tube) connected to a collection bath (8). The device further comprises a nozzle (6). In a particular embodiment of the methods of the invention, emulsion droplets ejected from the first reservoir (2) comprising the emulsion (3) by a nozzle (6), are guided by the inclined surface having a gradually changing slope towards the collection bath. The slope of the inclined surface (depicted as a tube with a curvature) starts vertically and ends at the collection bath (8) at an angle of about 20 degrees with the horizontal.

According to one aspect of the invention, devices are provided which allow particular post-processing of microparticles after inkjetting. The devices according to this aspect of the invention comprise an inclined surface (7) placed within or linked to a first reservoir (4) for holding the receiving fluid (5). The inclined surface (7) is placed such that droplets ejected from the nozzle (6) contact or land on the start of the slope of the inclined surface (7). As indicated above, the formed microparticles are extremely fragile and may be damaged by active post-treatments, e.g. by stirring the microparticles in the receiving fluid. According to the present invention devices are provided whereby the active post-treatment is postponed or omitted. More particularly, the devices are designed to ensure a passive post-treatment step, namely by allowing the ejected droplets to slide within the receiving fluid on an inclined surface (7). Most particularly, the devices of the present invention comprise an inclined surface, whereby the inclined surface has a slope of between 10 and 45 degrees, more particularly between 20 and 45 degrees. According to a further embodiment, the devices of the present invention have a gradually changing slope, starting vertically and ending with an angle of between 10 to 45 degrees. Examples of device according to particular embodiments of the invention are provided in FIGS. 1 and 2.

The methods and devices of the present invention allow the generation of populations of microparticles which are monodisperse, i.e. having a very narrow size distribution. Thus, a further aspect of the present invention relates to a population of monodisperse microparticles having a diameter of 1 to 100 µm, more particularly 2-50 µm, in particular 10 to 30 µm, even more particularly 10-20 µm. Within such a population more than 90% of the microparticles has a diameter which falls within 0.7 µM of the average value of said population. In particular embodiments, most particularly where a hydrogel polymer is used, the population is characterized by the fact that more than 90% of the microparticles have a diameter which falls within 0.5 µM of the average value of the population. In particular embodiments, within such population more than 90% of the microparticles has a diameter which falls within 4% of the average diameter. According to a particular embodiment, the microparticles are hydrogel polymer microparticles. According to a further embodiment, the microparticles contain a bioactive agent. According to a further embodiment, the microparticles contain a hydrophilic bio active agent.

The methods of the present invention wherein microparticles roll or slide on the inclined surface during initial swelling and/or hardening prevent damage to the particles such as occurring during collision of soft microparticles upon stirring. This subtle treatment has an advantageous effect on the overall shape of the microparticles as obtainable by the methods of the present invention, more particularly the methods are advantageous for obtaining an overall globular shape and/or smooth (non-dented) surface of the particles. Accordingly the present invention allows the manufacture of microparticle populations wherein less than 5%, more particularly less than 2% or most particularly even less than 1% of the particles of the population has a shape which deviates (more than 10%, more particularly more than 5%) from an overall globular shape, and/or has indentations and/or has other types of damaged surface.

A further aspect of the invention relates to the use of the microparticles of the invention for the administration of a bioactive agent to a mammal.

The microparticles of the present invention can be applied in a wide variety of medical applications. The microparticles can be incorporated in pharmaceutical compositions for parenteral and mucosal administration, such as oral administration; subcutaneous administration, intravenous administration, intra-arterial administration, intraperitoneal administration intramuscular administration, vaginal administration, and rectal administration.

The superior properties of the microparticles of the present invention makes them particularly suitable for applications whereby the size of the microparticle is critical, to avoid undesired effects. This is the case e.g. embolisation therapies, for example in the treatment of uterine fibroids. Other applications comprise the controlled release of bioactive agents, which are more accurately delivered as a result of the fact that the size of the microparticles wherein they are encapsulated is more homogeneous.

Thus, the present invention relates to methods of treatment comprising administering the microparticles of the present invention comprising a bioactive agent which is a therapeutic compound to a patient in need thereof. Additionally, the present invention relates to methods of diagnosis comprising administering the microparticles of the present invention comprising a bio active agent which is a contrast agent or marker to a patient to be diagnosed.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLES

Example 1

Figure 3:
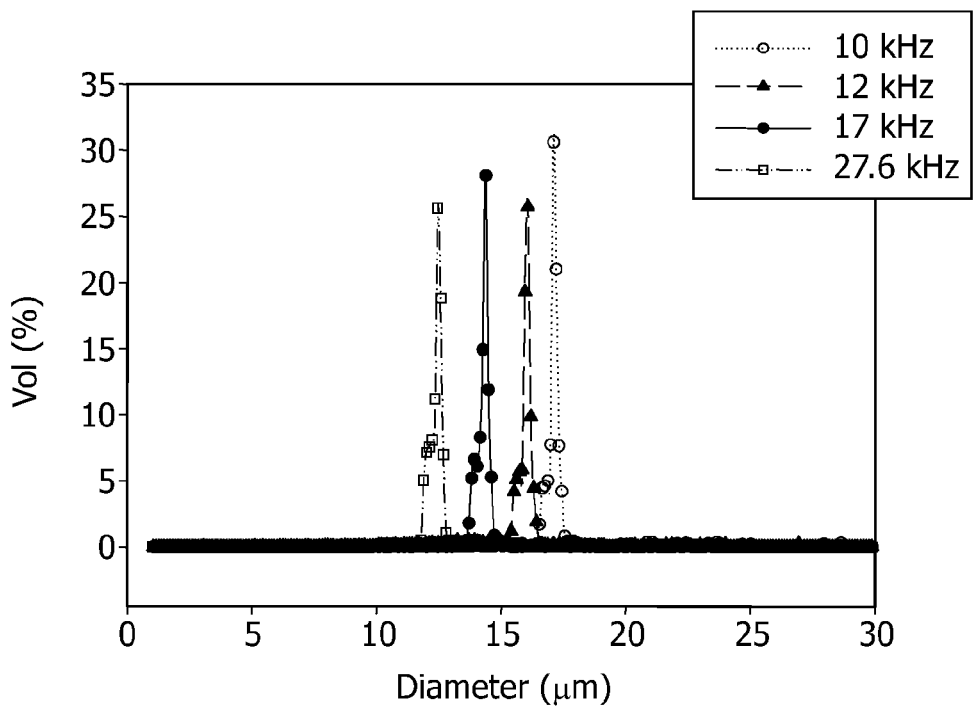
FIG. 3 shows the size distribution of particles prepared according to a particular embodiment of submerged inkjetting from a PEG-PBT (poly(ethylene oxide) terephthalate/(1, 4-butylene)terephthalate) solution of 1% in dichloroethane from a 20 μm nozzle at four different frequencies (open circles: 10 kHz; triangles: 12 kHz; filled circles: 17 kHz; squares: 27.6 kHz)

Injection of a PEGT/PBT Copolymer Emulsion from a 20 µM Nozzle, with Variation of the Frequency 1% PEGT-PBT solutions were inkjetted with a submerged microdrop nozzle into an aqueous solution comprising 0.3% pva 8/88. A 20 µm nozzle was used. Inkjetting was carried out for 10 minutes at a pressure of 1.5 bar and frequencies of 27.6, 17, 12 and 10 kHz. In the aqueous solution, an inclined surface was submerged and the droplets were allowed to move by rolling or sliding via this submerged surface into another container. There, the microparticles were left to settle, the supernatant was removed and the container was refilled with water. After stirring for 1-2 hours to remove the dichloroethane by dissolution into the aqueous phase the microparticles were measured on a Coulter multisizer III using a 50 µm orifice. Both volume weighted and number weighted modal diameters were 12.47, 14.39, 16.09 and 17.10 µm. The volume weighted average diameters were 12.40, 14.32, 15.60 and 17.05 µm. The size distributions are given in FIG. 3. The width of the peaks shows that over 90% of the particles (taking into account all counts of the Coulter counter between 10-20 microns) is within 0.5 µm of the average value.

Example 2

Injection of a PEGT/PBT Copolymer Double Emulsion

Figure 4:
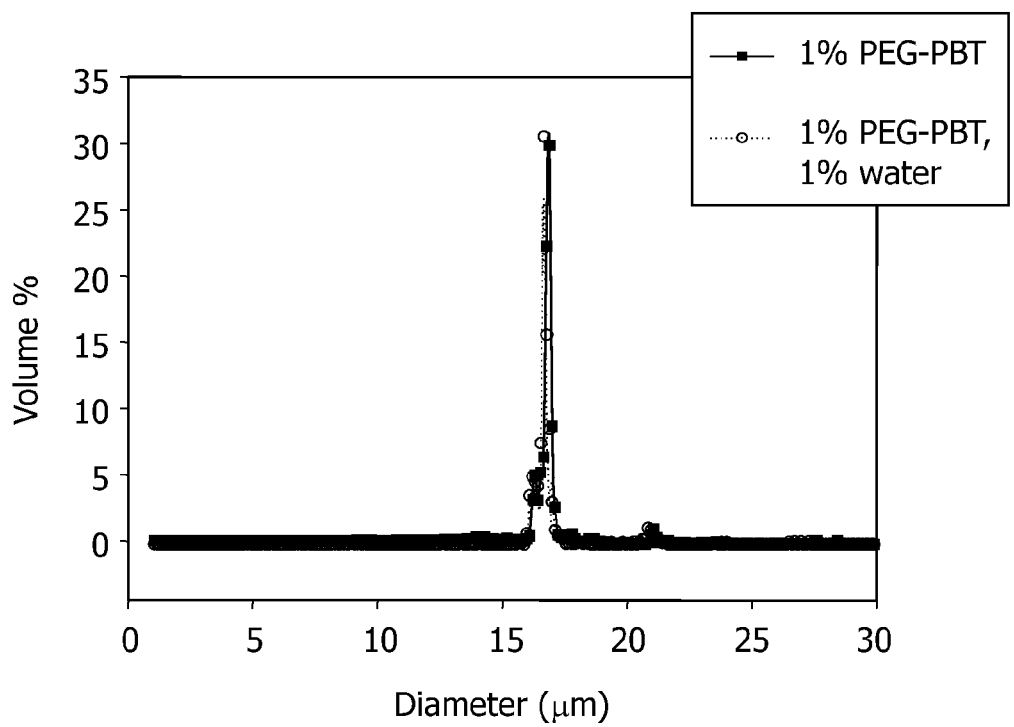
FIG. 4 shows the size distributions of particles prepared according to a particular embodiment of submerged inkjetting form a PEG-PBT solution of 1% in dichloromethane (filled squares) and the size distribution obtained by submerged inkjetting a primary emulsion containing 1% PEG-PBT, 1% water and 98% dichloromethane (open circles).
Figure 5:
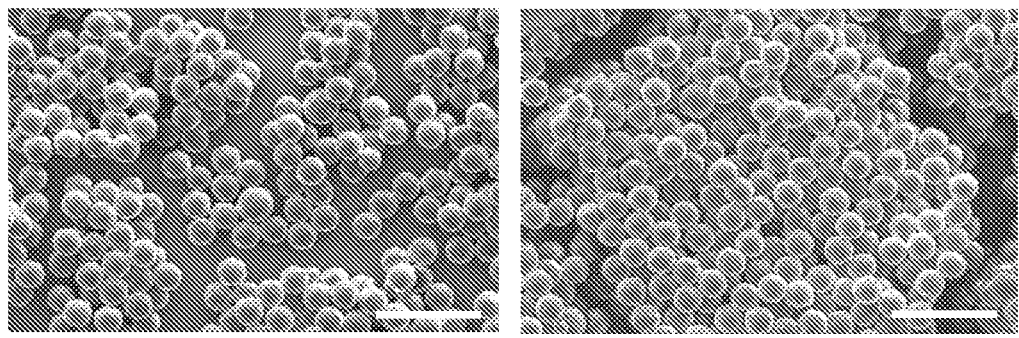
FIG. 5 shows SEM pictures of particles prepared according an particular embodiment of submerged inkjetting form a PEG-PBT solution of 1% in dichloromethane (left panel) and the size distribution obtained by submerged inkjetting a primary emulsion containing 1% PEG-PBT, 1% water and 98% dichloromethane (right panel). The bar at the right bottom represents 50 μm.

1% of water was added to a solution of 1% PEG-PBT in dichloromethane. The mixture was emulsified using an Ultraturrax for 60 seconds, yielding a strongly scattering emulsion. This emulsion was inkjetted using a submerged 30 µm nozzle at a frequency of 20.7 kHz and an assistant pressure of 0.45 bar into a an aqueous solution comprising 0.05% pva in a first container. As described in Example 1, the droplets were jetted into the aqueous solution onto a submerged inclined surface in the first container. The droplets gradually rolled or slided down the slope into a second container where they were left to settle. The supernatant was removed and the second container was refilled with water. After stirring for 1-2 hours to remove the dichloromethane by dissolution into the aqueous phase the microparticles were measured on a Coulter multisizer III using a 50 μm orifice. A reference sample was prepared from a 1% PEG-PBT solution, using the same pressure, frequency and receiving fluid. Size distributions of both samples are given in FIG. 4 and SEM pictures of the resulting particles are given in FIG. 5. Both for the double emulsion and for the reference particles over 90% of the particles are within 4% of the number averaged diameter.

Example 3

Inkjetting of Double Emulsion of PEGT-PBT: Incorporation of Fluorescent Protein

Figure 6:
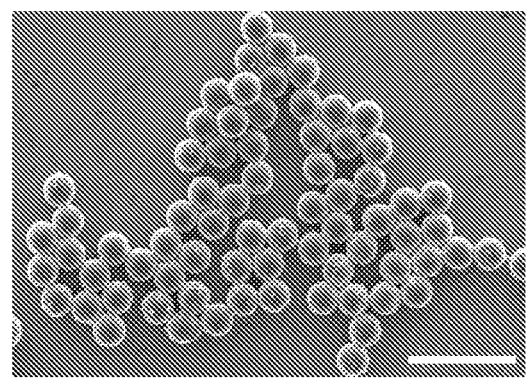
FIG. 6 shows SEM pictures of particles prepared according to a particular embodiment of submerged inkjetting form a PEG-PBT solution of 1% in dichloromethane without added stabilizer. The bar at the right bottom represents 50 μm.

The preparation of Example 2 was repeated with incorporation of a fluorescent protein. A FITC-modified mixture of proteins (fluorescent molecular weight standards F3526 of Sigma-Aldrich) was used. 1% of water containing the protein mixture was added to a 1% PEGT-PBT solution in dichloromethane. Immediately after inkjetting the shrinking of the particles was followed under the microscope and pictures were taken after the final size had been reached, as shown in FIG. 6.

Example 4

Inkjetting without an Added Stabilizer

Figure 7:
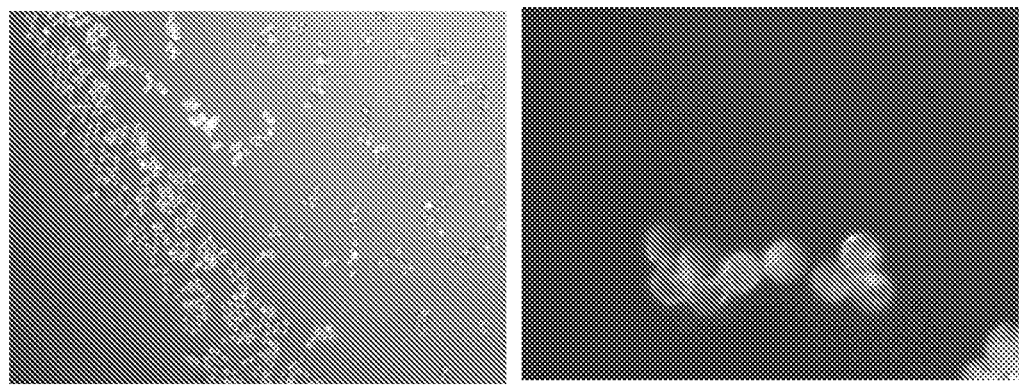
FIG. 7 shows fluorescence microscopy pictures of jetted microparticles prepared from a 1% PEG-PBT solution in dichloromethane with emulsified water incorporating a fluorescent protein at 10 and 50% magnification.

A 1% PEGT-PBT solution in dichloromethane was inkjetted using a submerged 30 μm nozzle at a frequency of 20.7 kHz and a assistant pressure of 0.45 bar into water without any further additives. After washing a sample was taken for an SEM photograph as shown in FIG. 7.

Example 5

Inkjetting Plga and Pla-Peo

Figure 8:
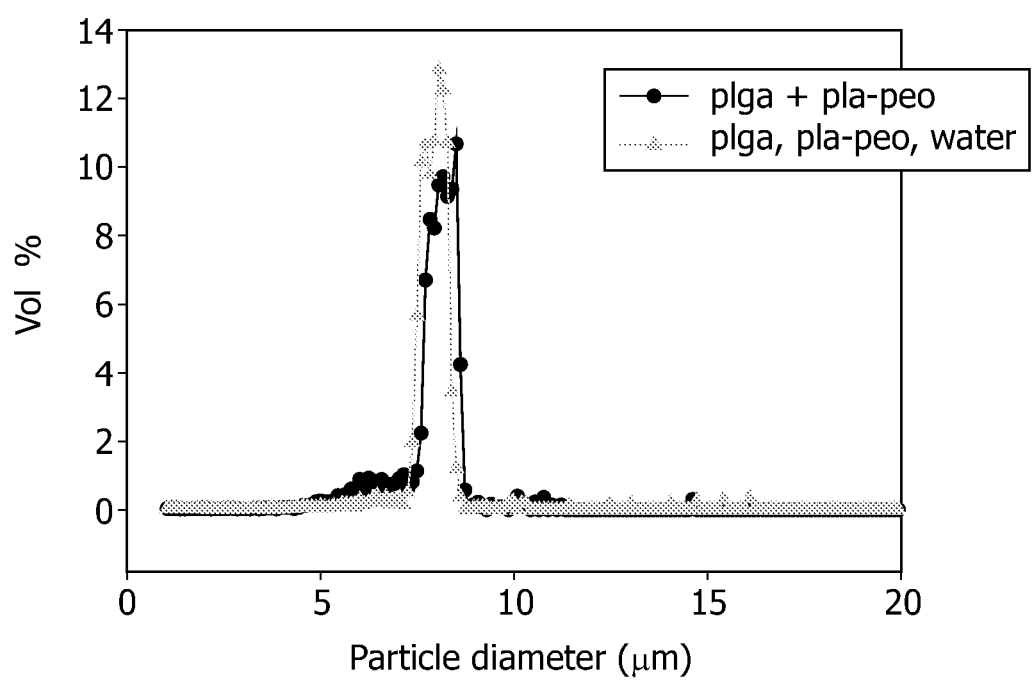
FIG. 8 shows size distributions of particles prepared by submerged inkjetting of dichloroethane containing 0.45% poly(lactic-co-glycolic acid (plga) and 0.35% Polylactic acid-polyethylene oxide (PLA-PEO) (black circles) and the size distribution obtained by submerged inkjetting of a primary emulsion containing 0.45% plga and 0.35% pla-peo and 0.5% water (grey triangles) in dichloroethane.

A solution (A) containing 0.35% pla-peo and 0.45% plga was inkjetted using a 20 micron nozzle in an aqueous 0.2% pva solution at a frequency of 15 kHz during 10 minutes. After inkjetting the product was washed twice and left stirring to evaporate the remaining solvent. The size distribution is shown in FIG. 8.

To solution (A) 0.5% of water was added containing 3% of the surfactant pluronic F127 and an emulsion was prepared by applying ultrasound. This led to a strongly scattering emulsion of water droplets in the polymer solution. The emulsion was inkjetted using a 20 micron nozzle in an aqueous 0.2% pva solution at a frequency of 15 kHz during 10 minutes. After inkjetting the product was washed twice and left stirring to evaporate the remaining solvent. The size distribution is shown in FIG. 8.

Example 6

Preparation of Iodinated Liquid Containing Capsules

Figure 9:
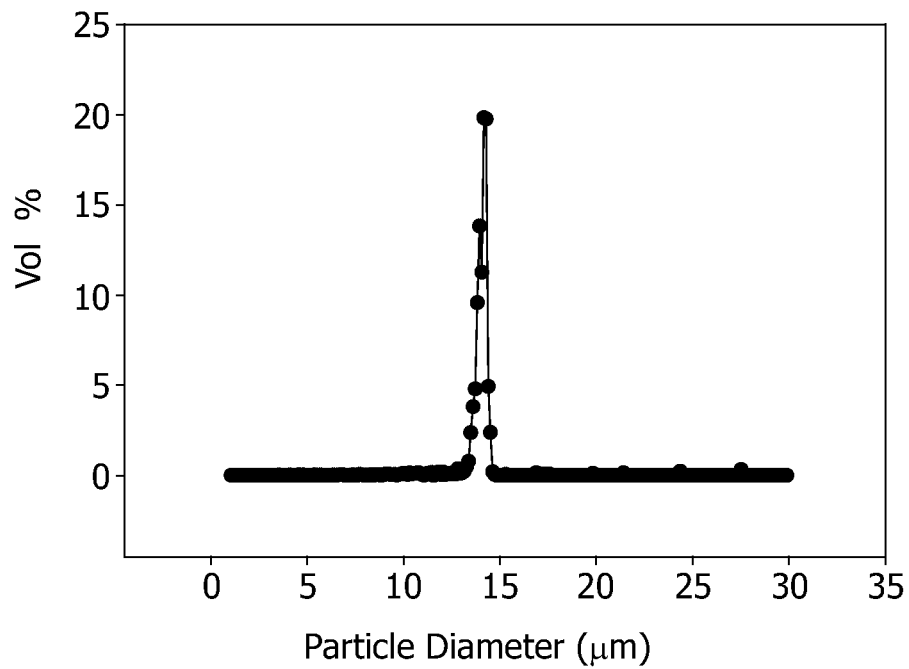
FIG. 9 shows the size distribution of plga polymer particles containing a iodinated oil, octan-2-yl 2,3,5-triiodobenzoate, obtained by submerged inkjet printing from a dichloroethane solution. The top panel shows the size distribution, the bottom panel shows the overall shape of representative particles.
Figure 9:
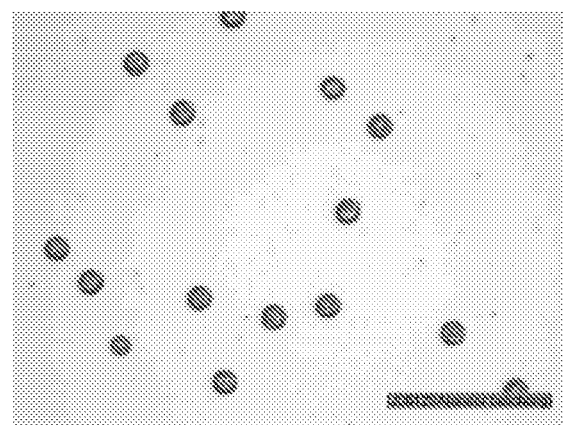

Octan-2-yl 2,3,5-triiodobenzoate containing 14 micron spheres were prepared by inkjetting a solution of plga and iodinated oil in dichloroethane into a 0.2% pva 8/88 solution at a speed of 15 kHz. The particle size distribution is shown in FIG. 9, a microscopy picture is given in FIG. 9*b*.

The invention claimed is:

1. A method for preparing monodisperse polymer microparticles with a size ranging between 1 and 100 μm, wherein said microparticles comprise a bioactive agent, said method comprising acts of:
   preparing an emulsion of said bioactive agent and a solution of a polymer;
   injecting particles of the emulsion from an inkjet nozzle submerged in an aqueous receiving fluid and operating at an assistant pressure and a given frequency; and
   hardening said particles into microparticles by allowing the particles to move, within the receiving fluid on an inclined surface, wherein the slope of said inclined surface is a gradually changing slope wherein the slope at each point has an angle of at least 10 degrees.

2. The method according to claim 1 wherein the polymer is a hydrogel polymer.

3. The method according to claim 2 wherein the hydrogel polymer has a hydration degree between 3 and 4.

4. The method according to claim 2, wherein the hardening act comprises allowing the particles to move, within the receiving fluid on said inclined surface for a time period which ensures the removal of solvent and saturation with water.

5. The method according to claim 1, wherein the concentration of the polymer in the emulsion is adjusted in order to obtain hydrogel particles with a diameter which is more than 40% of the diameter of the nozzle diameter.

6. The method according to claim 1, wherein the bioactive agent is hydrophobic.

7. The method according to claim 1, wherein said microparticles have a size ranging between 10 and 20 μm.

8. The method according to claim 1, wherein the polymer is a poly(ethylene oxide)terephthalate and poly(1,4-butylene) terephthalate (PEGT/PBT) copolymer.

9. The method according to claim 1, wherein the polymer is a hydrogel polymer and wherein the method is performed in the absence of stabilizer in the receiving fluid.

10. The method according to claim 1, wherein the inkjet nozzle is a piezo-driven inkjet nozzle.

11. The method according to claim 10, wherein the act of injecting particles comprises an act of driving the nozzle with a given pulse frequency.

12. The method according to claim 11, wherein the inkjet nozzle is driven with a pulse frequency of about 20 kHz.

13. The method according to claim 1, wherein the diameter of the inkjet nozzle is between 1 μm and 50 μm and the time period that the droplets are moved within the receiving fluid is between 2 and 60 seconds.

\* \* \* \* \*